(12) United States Patent
Leelamanit et al.

(10) Patent No.: US 6,484,053 B2
(45) Date of Patent: Nov. 19, 2002

(54) METHOD AND APPARATUS FOR TREATING POOR LARYNGEAL-ELEVATION DISORDER WITH SEQUENTIAL-HIGH VOLTAGE ELECTRICAL STIMULATION

(75) Inventors: Vitoon Leelamanit, Hatyai (TH); Chusak Limsakul, Hatyai (TH); Alan Geater, Hatyai (TH)

(73) Assignee: Pairash Thajchayapong, Bangkok (TH)

(*) Notice: Subject to any disclaimer, the term of this patent is extended or adjusted under 35 U.S.C. 154(b) by 94 days.

(21) Appl. No.: 09/725,055

(22) Filed: Nov. 29, 2000

(65) Prior Publication Data

US 2002/0133194 A1 Sep. 19, 2002

(51) Int. Cl.⁷ ................................................ A61N 1/00
(52) U.S. Cl. ............................................. 607/2; 607/62
(58) Field of Search ................................ 600/546, 593, 600/595; 607/2, 40, 72, 48, 62

(56) References Cited

U.S. PATENT DOCUMENTS 5,725,564 A * 3/1998 Freed et al.
5,891,185 A * 4/1999 Freed et al.
6,198,970 B1 * 3/2001 Freed et al.

* cited by examiner

Primary Examiner—Mark Bockelman

(57) ABSTRACT

The sequential stimulator for the treatment of dysphagic patients incorporates a unit which is capable of detecting a swallowing signal from the glossal or temporalis surface electromyography (SEMG). When a swallowing signal is recognized, a trigger signal is sent to the stimulation generation unit to release high voltage stimuli sequentially to the suprahyoid muscles or the masseter muscles and the pharyngeal muscles in order to assist in the elevation of the larynx. This enables the pharyngeal lumen to open more widely so that food can pass through the patient's pharynx and into the oesophagus more easily during swallowing. Thus the sequential stimulator is a device for assisting swallowing in patients with dysphagia due to a variety of causes, for instance, brain injury, cerebrovascular accident, injury of the cervical nerves, muscles weakness, or old age. The stimulator is operative only when the patient attempts to swallow and provides a physiologic stimulus and provides a means of immediate relief of the swallowing difficulty. The device is also useful for physical therapy whereby the muscles under the chin, the masseter muscles and the pharyngeal muscles can be re-educated to contract in the normal coordinated sequence.

18 Claims, 5 Drawing Sheets

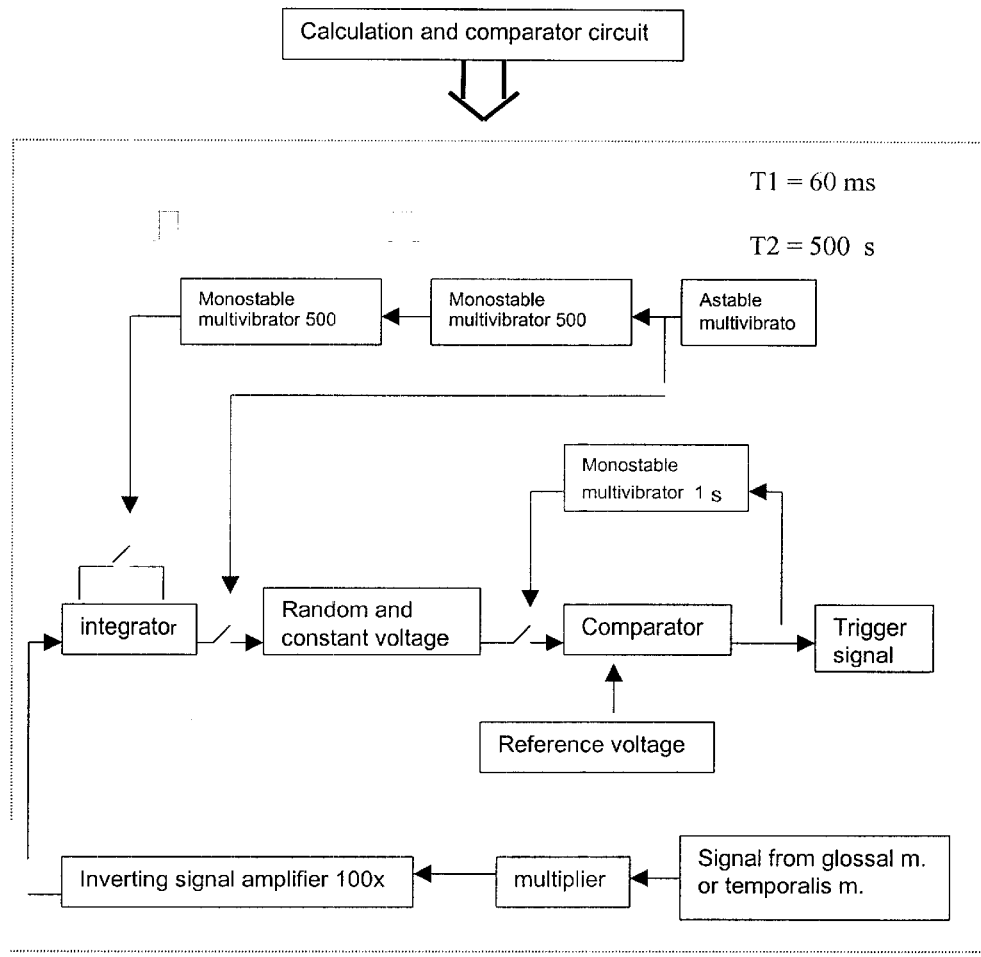
Figure 3.
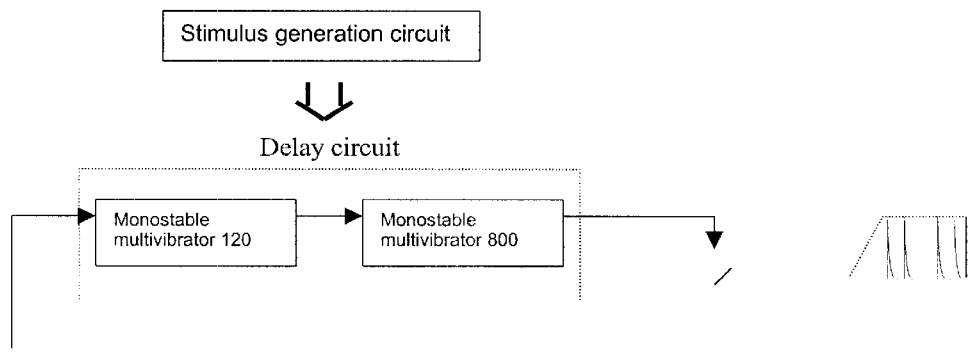

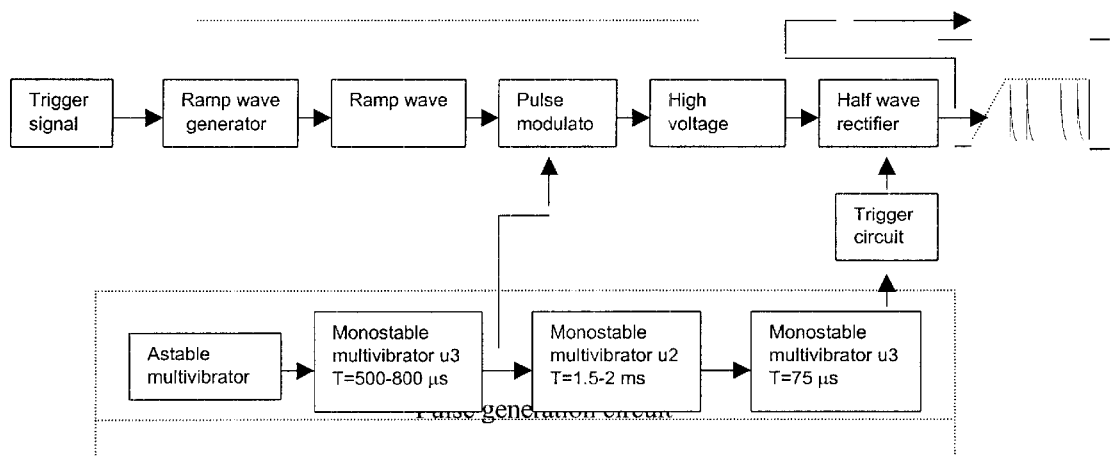
Figure 4.
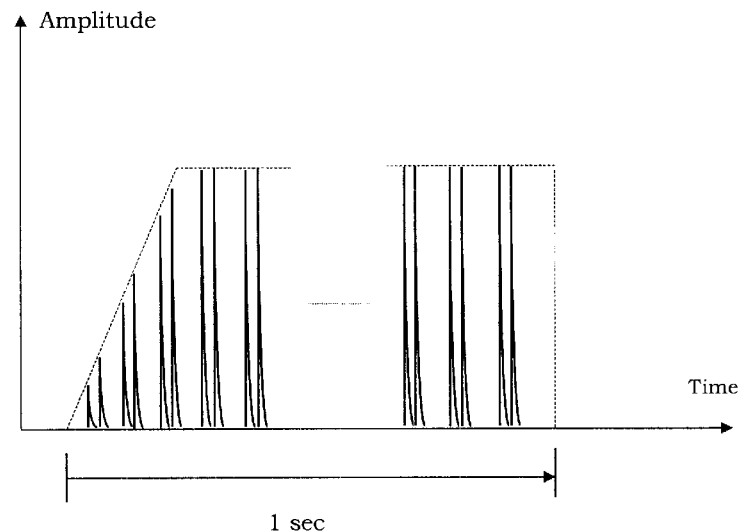
Figure 5.
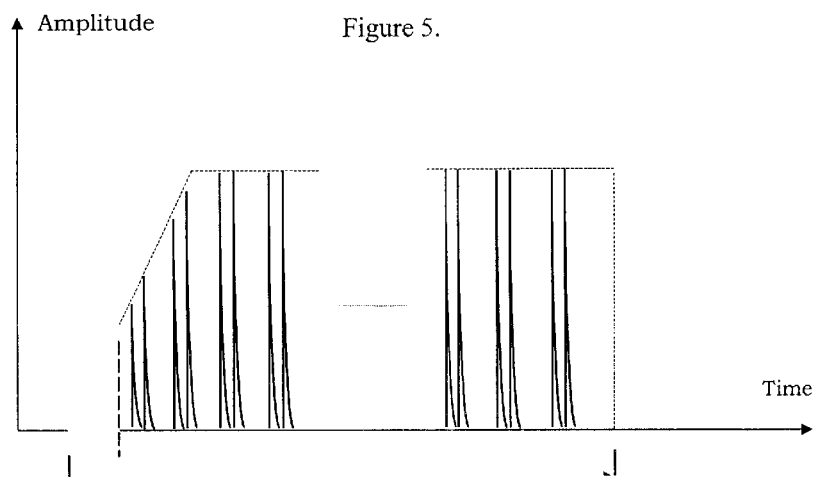

METHOD AND APPARATUS FOR TREATING POOR LARYNGEAL-ELEVATION DISORDER WITH SEQUENTIAL-HIGH VOLTAGE ELECTRICAL STIMULATION

BACKGROUND OF THE INVENTION

1. Field of the Invention

The present invention relates generally to a method and an apparatus for treating poor laryngeal-elevation disorder with sequential-high voltage electrical stimulation.

2. Description of the Prior Art

The mechanism of normal human swallowing involves 3 phases:

Phase 1: is the oral phase, during which food in the oral cavity is masticated and mixed.

Phase 2: is the pharyngeal phase, during which the masticated and mixed food bolus is propelled from the oral cavity into the pharyngeal lumen and thence into the upper oesophagus. The second phase of swallowing involves the use of the glossal muscles and the pharyngeal muscles (suprahyoid and thyrohyoid) and a lowering of the base of the tongue. The tongue muscles then propel food bolus from the oral cavity into the pharyngeal lumen. At this stage, the muscles of the pharynx contract in sequence, raising elevating the larynx and moving it forward in order to open the pharyngeal lumen and the upper oesophageal sphincter so that the bolus can pass readily into the upper oesophagus.

Phase 3: is the oesophageal phase and marks the phase of peristaltic propulsion of the bolus through the oesophagus and into the stomach.

There are many different treatment modalities for dysphagic patients depending on the pathology of the patient. For instance, in patients who have difficulty with the initiation of swallowing, the swallowing reflex may be stimulated by a special device (U.S. Pat. No. 5,891,185) or by the use of a cooled dental mirror to stroke the anterior tonsillar pillar.

For patients in whom the function of the pharyngeal muscles is absent, reduced or uncoordinated, laryngeal elevation may be insufficient or absent. This has the effect of reducing the width of the pharyngeal lumen and an inadequate opening of the upper oesophageal sphincter. The patient therefore experiences difficulty in swallowing or may aspirate food into the larynx and the trachea. Such patients may be treated with several methods such as, for instance, exercise of the pharyngeal muscles using various biofeedback devices which enhance contraction of the pharyngeal muscles, or surgery to retract the larynx to the mandible, to close the larynx, or to resect the upper oesophageal sphincter. None of these treatments offers an automatic and dynamic cure, i.e., a means to increase the function of the pharyngeal muscles and aid in the elevation of the larynx actually during the swallow.

Treatment of patients with dysphagia associated with dysfunction of the pharyngeal muscles using previously available high voltage stimulators, which are non-automatic and which are applied during regular sessions, is able to increase the power of contraction of the pharyngeal muscles and suprahyoid and reduce the symptoms of patients with mild dysphagia, but is ineffective for severely dysphagic patients or those who aspirate when swallowing.

During development of the sequential stimulator for treatment of dysphagic patients emphasis was placed on the need to provide physiological stimulation of the muscles of deglutition, i.e, providing stimulation only at the time that the patient attempts to make an actual swallow, instead of during regular sessions of physical therapy. The device, therefore, is neither intended nor capable of initiating swallowing. Instead it has the capability to detect when the patient makes an attempt to swallow and responds by sending a sequence of high voltage stimuli to the muscles of the suprahyoid and the thyrohyoid muscles, whose contraction elevates the larynx and opens the pharyngeal lumen in order to allow the food bolus to pass through the pharynx. The device thus reinforces the normal process during swallowing, and is of particular value for the treatment of dysphagia due to the central nervous system lesions, or where immediate restoration is needed, for instance, in cerebrovascular accident, muscle weakness due to aging, and disruption of normal motor pathways.

SUMMARY OF THE INVENTION

The purpose of this invention is to provide sequential electrical stimulation for the treatment of dysphagic patients. The invention comprises 2 functional entities. The first functional entity of the device is responsible for monitoring the electrical signal from the glossal muscle picked up using skin surface electrodes placed bilaterally in the area of the patient's submandibular salivary glands or from the temporalis muscle picked up using skin surface electrodes placed bilaterally in the patient's temporal region. The surface electromyographic signal is then passed to a circuit responsible for detecting an attempted swallowing event. When an attempted swallowing event is detected, a trigger signal is sent to the second functional entity of the device, which is responsible for generating a high voltage pulsed stimulus which is delivered to the suprahyoid or masseter muscles and the thyrohyoid muscle. Contraction of these muscles in response to stimulation has the effect of elevating the larynx and when this occurs the pharyngeal lumen is widened, thereby allowing the easy passage of the food bolus through the pharynx into the upper oesophagus. Thus the sequential stimulator for treatment of dysphagic patients assists the normal physiological mechanism of swallowing, and does so at the moment when the patient attempts to perform a swallow.

The sequential stimulator for the treatment of dysphagic patients comprises a unit which is capable of detecting a swallowing signal from the glossal or temporalis surface electromyograph (SEMG). When a swallowing signal is recognized, a trigger signal is sent to the stimulation generation unit to release high voltage stimuli sequentially to the suprahyoid muscles or the masseter muscles and the pharyngeal muscles in order to assist in the elevation of the larynx. This enables the pharyngeal lumen to open more widely so that food can pass through the patient's pharynx and into the oesophagus more easily during swallowing. Thus the sequential stimulator is a device for assisting swallowing in patients with dysphagia due to a variety of causes, for instance, brain injury, cerebrovascular accident, injury of the cervical nerves, muscles weakness, or old age. The stimulator is operative only when the patient attempts to swallow and provides a physiologic stimulus and provides a means of immediate relief of the swallowing difficulty. However, the device is also useful for physical therapy whereby the muscles under the chin, the masseter muscles and the pharyngeal muscles can be re-educated to contract in the normal coordinated sequence.

BRIEF DESCRIPTION OF THE DRAWINGS

The invention will be further described in conjunction with the accompanying drawings, in which.

DETAILED DESCRIPTION OF THE PREFERRED EMBODIMENTS

Figure 1:
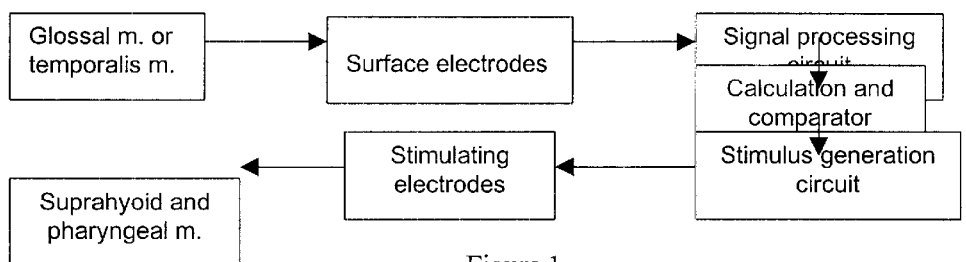
FIG. 1 shows components of a sequential electrical stimulator according to the present invention.

The sequential stimulator for treatment of dysphagic patients comprises two functional entities, the first to monitor SEMG and detect an attempted swallowing event and the second to produce a sequential high voltage stimuli to stimulate the muscles of swallowing. The first entity comprises surface electrodes, a signal processing circuit and a circuit for calculation and comparator (FIG. 1). The second entity comprises a stimulus generation circuit and electrodes to deliver the stimulus to the muscles of swallowing. These entities and their component circuits are described in detail below.

1. Surface Electrodes

The cup-shaped surface electrodes are made of gold-plated silver and are 0.5–1 cm in diameter. They are placed bilaterally either over the area of the submandibular salivary glands in order to pick up the surface electromyographic signal from the glossal muscle or in the temporal region to pick up the SEMG from the temporalis muscles. A plate ground electrode in placed on the inner aspect of the right forearm.

2. Signal-processing Circuit

Figure 2:
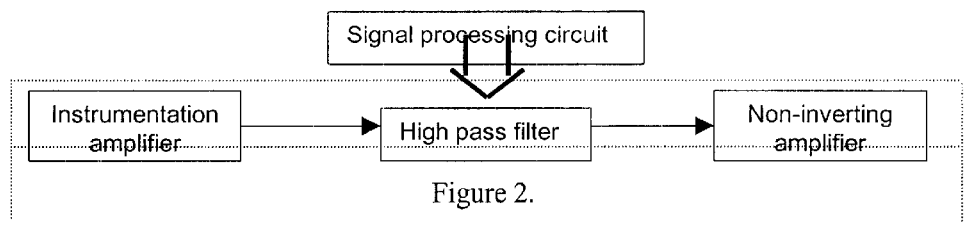
FIG. 2 shows the signal processing circuit in the sequential electrical stimulator of FIG. 1.

This comprises various coordinated component circuits, as shown in FIG. 2. These are the instrumentation amplifier, the high-pass filter, and the non-inverting amplification circuit. The signal from the glossal or temporalis muscles picked up by the surface electrodes (item 1 above) is amplified using the instrumentation amplifier set to a gain of 100. The DC component of the signal is then filtered out by the high-pass filter set at a cut-off of approximately 5 Hz, amplified by the non-inverting amplifier set to a gain of 10, and then passed on to the calculation and comparator circuit.

3. Calculation and Comparator Circuit

The calculation and comparator circuit is responsible for calculation of the power of the signal received from the signal processing unit (item 2 above). Power is calculated according to the following equation $$P = \frac{1}{(4.7 \text{ ms})} \int_0^t v^2 dt \qquad 1$$

where P=signal power, v is the amplitude of the signal from the glossal or temporalis muscles and t is time ranging from 60–120 ms.

Figure 3:
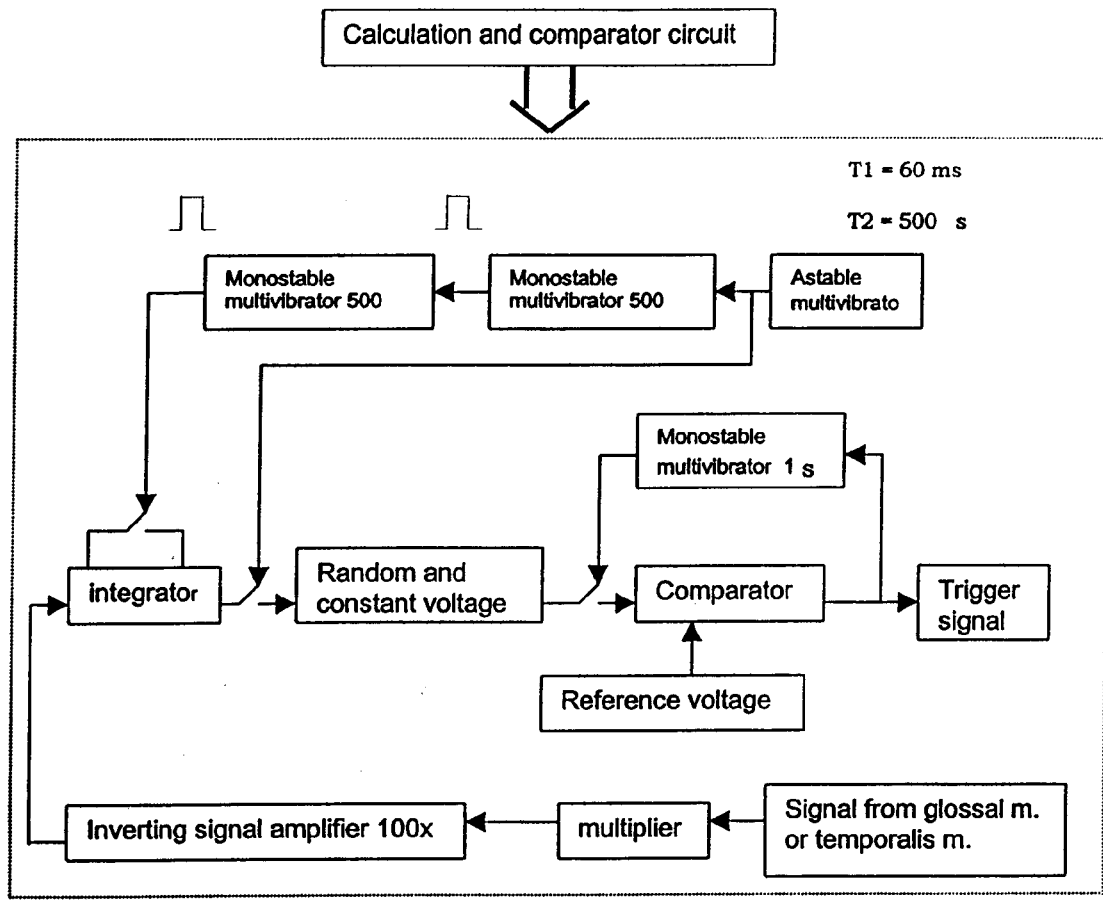
FIG. 3 shows components of the calculation and comparator circuit in the sequential electrical stimulator of FIG. 1.

The calculation circuit first calculates the square of the signal from the signal processing circuit (item 2 above), then performs an integration to calculate the mean power according to equation (1) above (FIG. 3). The resulting signal is then passed to the comparator where it is compared with a reference voltage adjustable over the range 0–2 volts. If the power signal exceeds the reference the comparator output goes high, causing the monostable multivibrator circuit to produce a pulse of width 1–3 seconds which triggers the stimulus generation circuit and at the same time switches off the calculation circuit to prevent calculation during the period of stimulation.

When the power signal is lower than the reference, the comparator circuit output goes low and therefore the monostable multivibrator no longer triggers the stimulus-generation circuit.

4. Stimulus Generation Circuit

Figure 4:
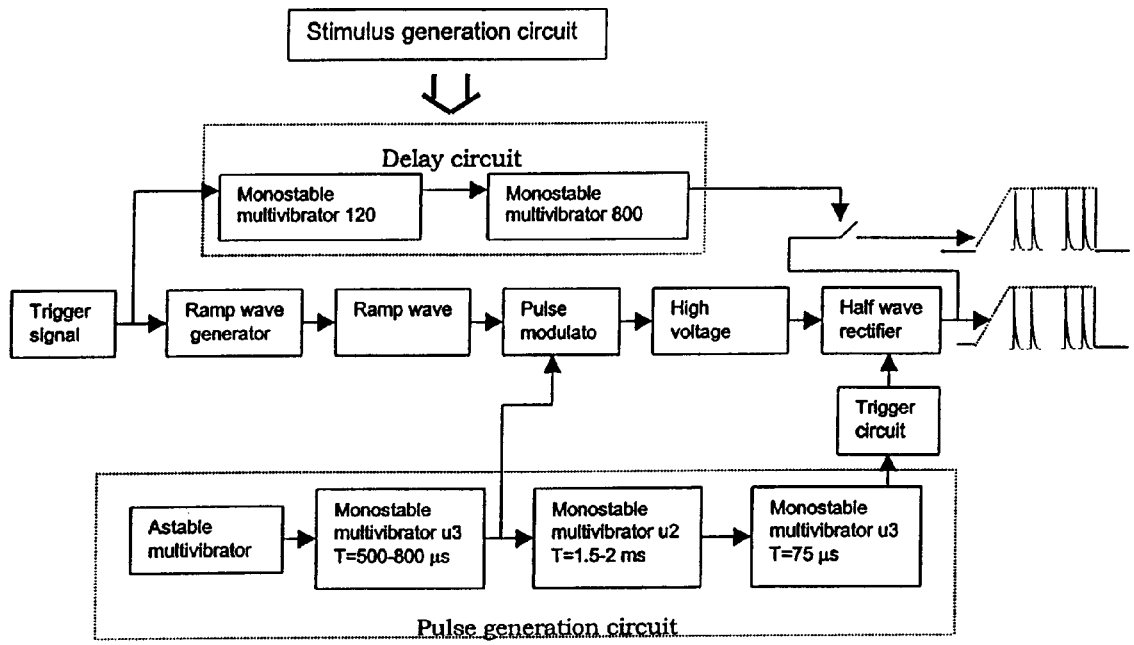
FIG. 4 shows components of the stimulus generation circuit in the sequential electrical stimulator of FIG. 1.
Figure 5:
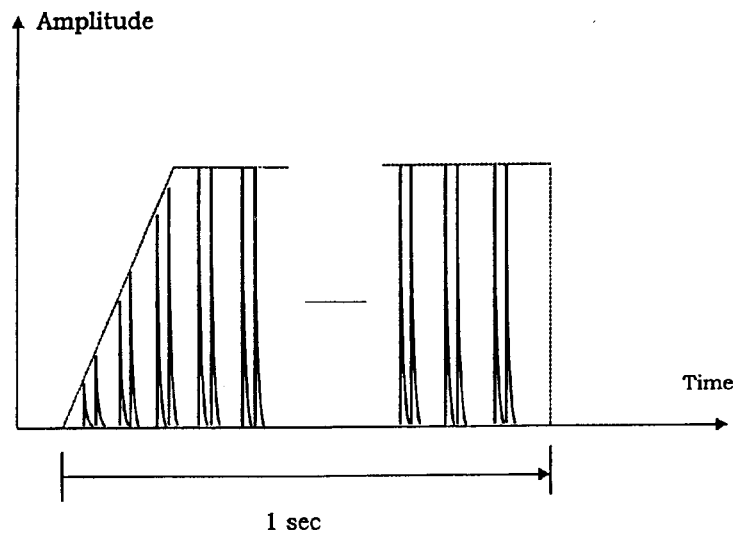
FIG. 5 shows stimulus in channel 1 applied to the muscles below the chin or masseter muscles according to the present invention.
Figure 6:
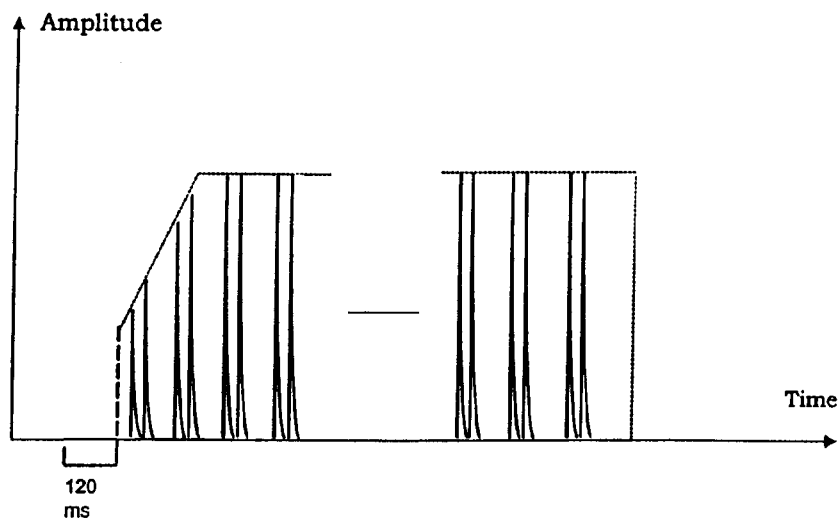
Figure 7:
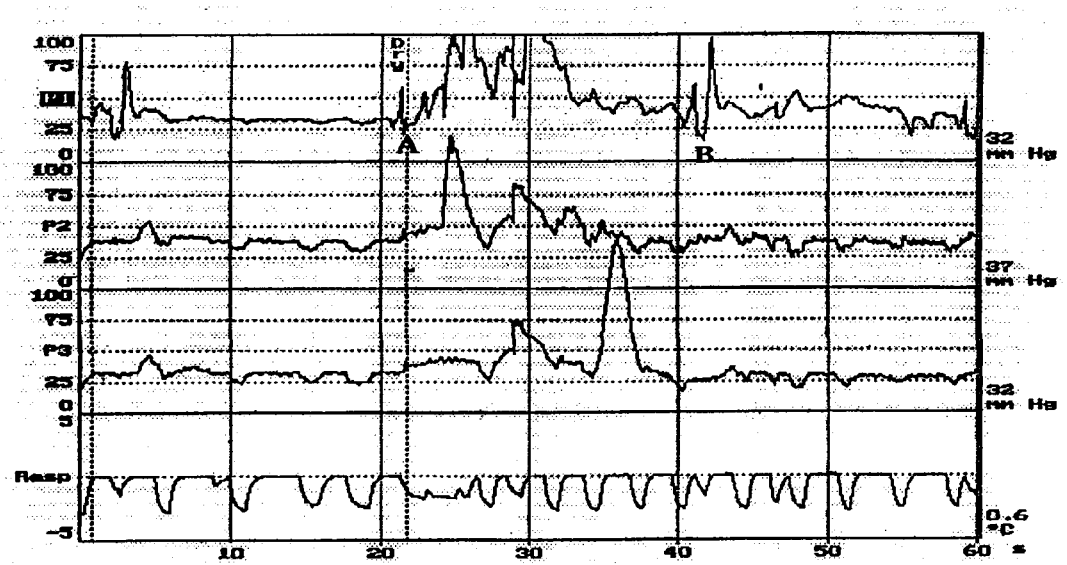

The circuit generates a stimulus when it receives the trigger stimulus from the calculation and comparator circuit (item 3 above). The generated stimulus is a twin peak pulse (FIG. 4) of width not greater than 75 s and frequency of 40–80 Hz. The amplitude of successive pulses gradually increases over the first 250 ms, and thereafter remains at a constant level, which can be adjusted in the range of 0–250 volts. The overall duration of stimulation can be adjusted in the range 1–3 s (FIG. 5). The device is fitted with a by-pass button to trigger the stimulation-generation circuit independently of the afferent signal from the patient, which can be used to set the stimulation parameters appropriate for the individual patient.

Figure 6:
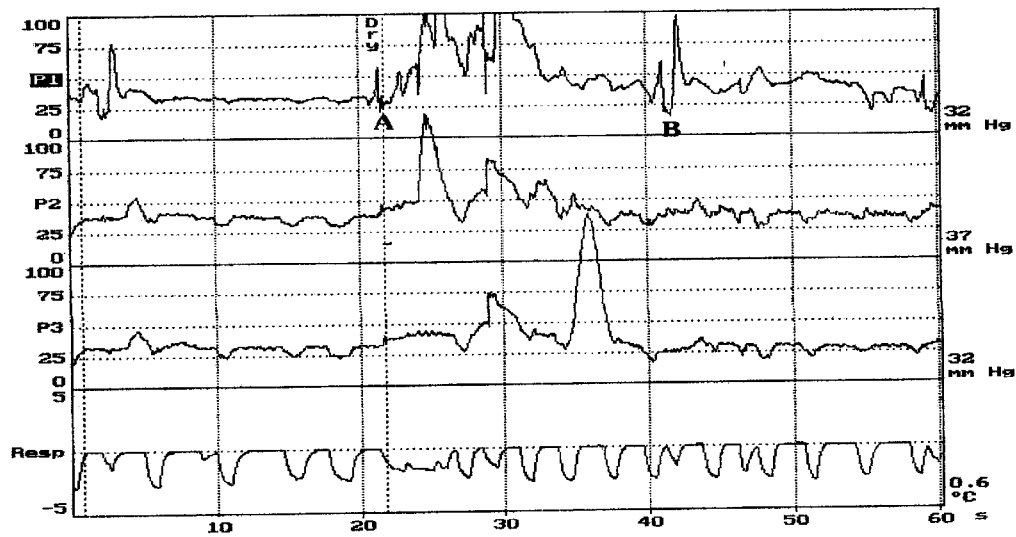
FIG. 6 shows stimulus in channel 2 applied to the pharyngeal muscles (thyrohyoid) according to the present invention.

The generated stimulus is available on 2 channels. The onset of the stimulus in the first channel occurs immediately upon receipt of the trigger stimulus, while that in the second channel is subject to a delay of 120 ms (FIG. 6). The delay circuit can be adjusted in the range 0–2 s. The stimulus in each channel is passed to a pair of rubber-carbon composite electrodes of various sizes ranging from 0.5 in×0.5 in to 1 in×1 in. The electrodes connected to channel 1 are placed in the midline submental position and above the hyoid or on the skin at the side of the cheek in the area above the masseter muscle. Those connected to channel 2 are placed, one at each side, in the region of the wings of the thyroid cartilage.

The following example provides further illustration of the application of the invention.

Results of testing the sequential stimulator to treat patients with dysphagia due to poor elevation of the larynx.

Thirteen severely dysphagic patients accompanied by aspiration were examined using 1. pharyngoesophageal manometry
2. x-ray videofluoroscopy to confirm that the swallowing dysfunction was due to poor elevation of the larynx. The patients were then treated using the sequential stimulator to assist in the elevation of the larynx during swallowing. The results of treatment were evaluated by comparing the characteristics of swallowing before, during and after application of the device. Other, longer-term, parameters were also considered, including the volume of food taken at each meal, the time taken to eat food, and body weight.

Patients were considered to show improvement during use of the device if they fulfilled any of the following:
1. Reduction in dysphagic symptoms and ability to swallow larger volumes with no coughing or aspiration;
2. First rise in the M wave during examination by pharyngoesophageal manometry showed increased amplitude;
3. Fall in the level of the pharyngoesophageal pressure recording following elevation of the larynx to a level approaching zero;
4. Width of the pharyngeal lumen as revealed using x-ray videofluoroscopy increased.

Late effects were evaluated on the basis of the following criteria:
1. Volume of food per meal and number of meals per day increased;
2. Reduced time taken for eating a meal;
3. Increased body weight;
4. Delayed return of dysphagic symptoms.

Figure 7:
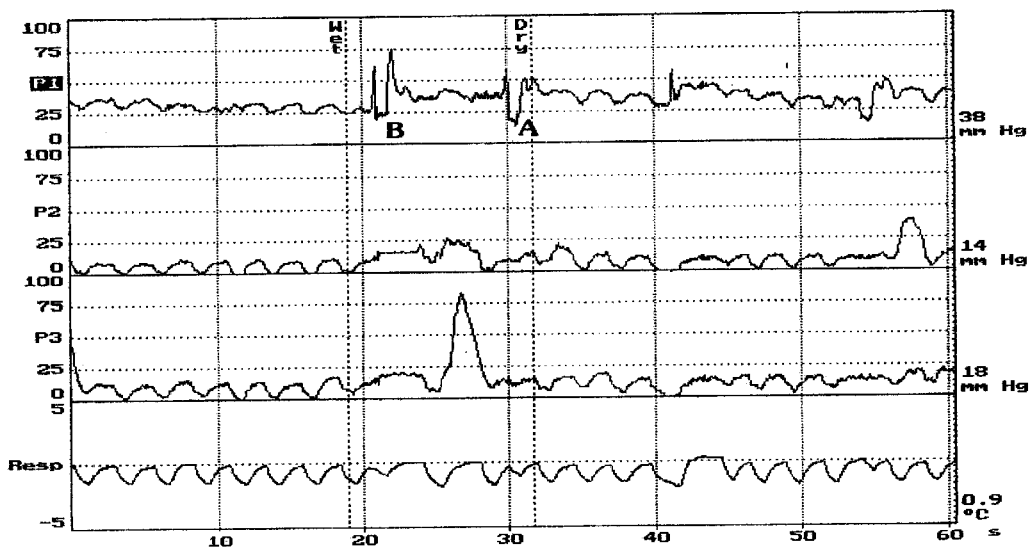
FIG. 7 shows recording of intrapharyngeal pressure in the region of the cricopharyngeus of a patient during a dry swallow, showing the relatively low initial increase of M wave (A) and the intrapharyngeal pressure not approaching zero. The patient has to repeat the attempt to swallow several times before she is actually able to swallow (B).
Figure 1:
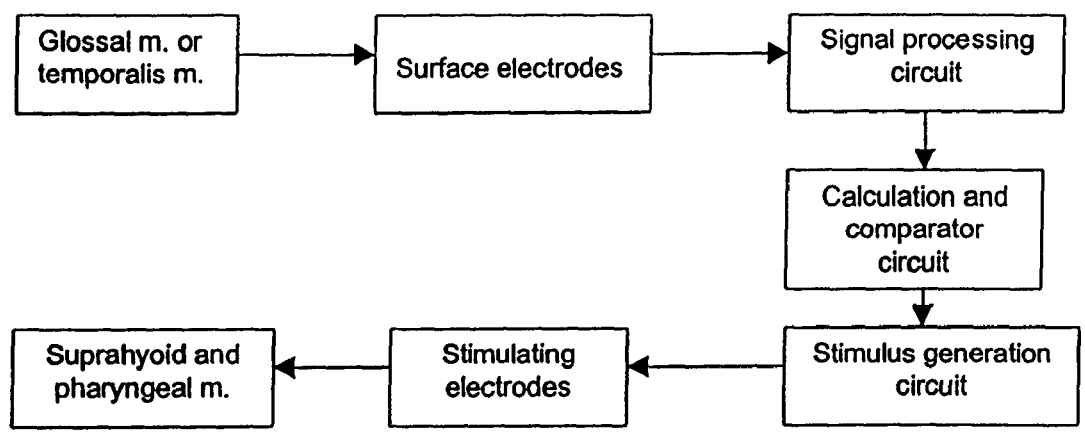
Figure 2:
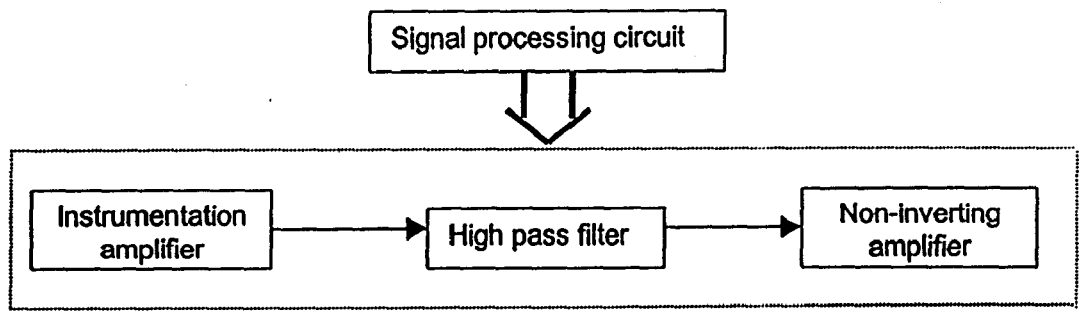
Figure 8:
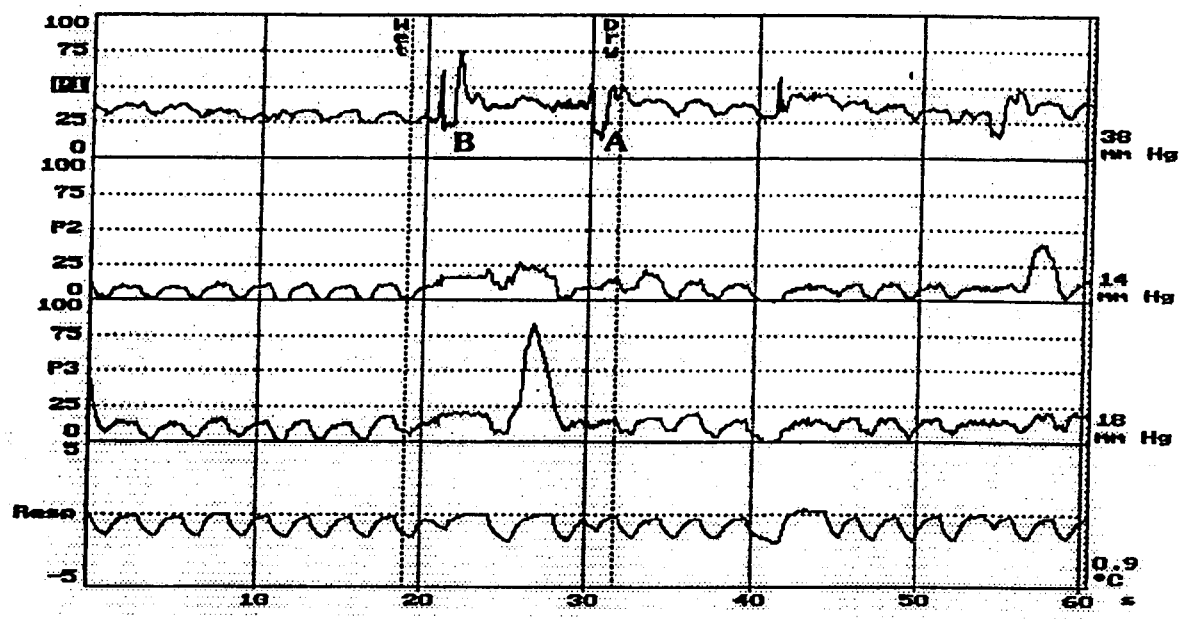
FIG. 8 shows recording of intrapharyngeal pressure in the region of the cricopharyngeus of the same patient in FIG. 7 during a dry (A) and wet (B) swallows while using the sequential-high voltage electrical stimulator, showing the improved initial increase of M wave and the intrapharyngeal pressure approaching zero. The patient can make a successful swallow in only one attempt.

The 13 patients comprised 6 males and 7 females, aged 35–87 years, with a mean age of 57 years. The causes of the dysphagia were related to brain injury in 2 patients, surgery of the intervertebral disk of the cervical spine in 1 patient, chronic alcoholism in 1 patient, syringomyelia in 1 patient, old age in 7 patients, and radiotherapy for cancer of the neck in 1 patient. Eleven patients showed immediate improvement of symptoms during use of the device, one showed no improvement but after using the sequential stimulator it was found to have been inoperative. In one patient the muscle was fibrosed as a result of radiotherapy and was unable to respond to stimulation. The immediate improvement of symptoms was confirmed by manometric examination (FIGS. 7 and 8) and x-ray videofluoroscopy. The patients could swallow increased volumes of water without aspiration. The late effects of treatment were found to depend on the number of times the patient had used the sequential stimulator and the duration of use each time. For example, a patient using the sequential stimulator for the third time experienced a reduction in dysphagic symptoms for a longer period than after the first time of use. Similarly, a patient using the sequential stimulator for 8 hours experienced a greater reduction in symptoms than when using it for only 4 hours.

Before initiating treatment, a blood specimen from every patient was taken to test for diabetes mellitus and abnormality of the thyroid hormones, in order to identify patient with dysphagia associated with these conditions. All 13 patients received initial treatment with vitamin B1-6-12 and calcium gluconate for one month in order to treat dysphagia which may have been responsive to medical treatment and to ensure that neither medical treatment caused any improvement in the symptoms. Only then was the treatment with the sequential stimulator started.

INDUSTRIAL APPLICATION

1. The sequential stimulator for treatment of dysphagic patients could be manufactured in desk-top or floor-standing versions in order to treat dysphagic patients who are immobile.
2. The sequential stimulator for treatment of dysphagic patients could be manufactured in a small, lightweight, ambulatory version for treatment and use in assisting swallowing during eating by ambulatory patients.
3. The sequential stimulator for treatment of dysphagic patients could be manufactured in modified versions suitable for other types of high voltage electrical stimulation to assist the working of other dysfunctional muscles.

What is claimed is:

1. A method for treating a dysphagic patient using variable high voltage sequential electrical stimulation comprising the steps of:
   detecting a swallowing signal from the SEMG of the glossal or temporalis muscle of the patient during a swallowing event with at least a pair of electrodes placed bilaterally on the skin in the region of the submandibular salivary glands of the patient or bilaterally in the temporal area, and a ground electrode placed on the inner right forearm of the patient;
   processing the signal from the electrodes with a signal processing circuit for amplifying and passing the signal to a calculation and comparator circuit;
   calculating the signal and comparing the signal with the calculation and comparator circuit using a reference to determine whether the patient is attempting to swallow, whereby an attempted swallow is recognised and a signal will be sent to a stimulation generation circuit to deliver high voltage stimuli to the patient's muscles under the chin and of the pharynx via stimulation electrodes placed under the chin and on the pharynx of the patient; and
   generating high voltage by the stimulation generation circuit which delivers high voltage stimuli to the patient's muscles under the chin and pharyngeal muscles via electrodes connected to at least one channel.

2. The method for treating a dysphagic patient using variable high voltage sequential electrical stimulation according to claim 1, wherein said electrodes connected to more than one channel and the stimulus in the channels are sent simultaneously.

3. The method for treating a dysphagic patient using variable high voltage sequential electrical stimulation according to claim 1 wherein the step of performing and calculating the signal includes the steps of:
   performing a calculation to determine the power of the signal of the glossal muscles of the patient with the following equation:

$$P = \frac{1}{(4.7 \text{ ms})} \int_0^t v^2 dt$$

Wherein P is the power of the signal from the glossal or temporalis muscles, v is the amplitude of the SEMG signal after passing through the signal processing circuit, and t is the time, ranging from 60–120 ms.;
   comparing the power signal P with a reference voltage, which is adjustable over the range 0–2 volts; and
   generating an adjustable pulse signal of width 1–3 seconds if said calculated power signal has a value higher than said reference voltage.

4. The method for treating a dysphagic patient using variable high voltage sequential electrical stimulation of claim 3 further comprising the step of:
   sending the adjustable pulse signal to said stimulation generation circuit to activate the stimulation generation circuit and stop operation of the calculation and comparator circuit during the generation of the stimulus.

5. The method for treating a dysphagic patient using variable high voltage sequential electrical stimulation according to claim 1 further comprising the step of:
   sending the adjustable pulse signal to said stimulation generation circuit to activate the stimulation generation circuit and stop operation of the calculation and comparator circuit during the generation of the stimulus.

6. A sequential electrical stimulator comprising:

a detecting swallowing signal circuit for detecting the signal from the SEMG of the glossal or temporalis muscle of a patient during a swallowing event with at least a pair of electrodes placed bilaterally on the skin in the region of the submandibular salivary glands of the patient or bilaterally in the temporal area, and a ground electrode placed on the inner right forearm of the patient;

a signal processing circuit for amplifying and passing the signal to the calculation and comparator circuit;

a calculation and comparator circuit for performing calculation and comparison for performing a calculation to determine the power of the signal of the glossal muscles of the patient with the following equation:

$$P = \frac{1}{(4.7 \text{ ms})} \int_0^t v^2 dt$$

wherein P is the power of the signal from the glossal or temporalis muscles, v is the amplitude of the SEMG signal after passing through the signal processing circuit, and t is the time ranging from 60–120 ms., comparing the power signal P with a reference voltage, which is adjustable over the range 0–2 volts, and generating an adjustable pulse signal of width 1–3 seconds if said calculated power signal has a value higher than said reference voltage; and a stimulation generation circuit having at least 2 or more output channels generating a high-voltage twin-peak pulse signal of width 75 s and frequency 40–80 Hz with a gradually increasing amplitude until the constant value is reached after 250 ms to the patient's under chin muscles and pharyngeal muscles via electrodes connected to several different channels or at least one output channel.

7. The sequential electrical stimulator according to claim 6, wherein the stimulus signal in one of the channels is delayed by between 0–120 ms after the stimulus signal in one other channel.

8. The sequential electrical stimulator according to claim 7, wherein the high-voltage twin-peak stimulation generation circuit generates stimulation signals in each channel with variable speeds.

9. The sequential electrical stimulator according to claim 6, wherein the high-voltage twin-peak stimulation generation circuit has at least two channels.

10. The sequential electrical stimulator according to claim 9, wherein each of the channels delivers stimulation signals no faster than one per 120 ms.

11. The sequential electrical stimulator according to claim 10, wherein the high-voltage twin-peak stimulation generation circuit generates stimulation signals in each channel with variable speeds.

12. The sequential electrical stimulator according to claim 9, wherein the high-voltage twin-peak stimulation generation circuit generates stimulation signals in each channel with variable speeds.

13. The sequential electrical stimulator according to claim 6, wherein the high-voltage twin-peak stimulation generation circuit generates stimulation signals in each channel with variable speeds.

14. The sequential electrical stimulator according to claim 6, further comprising a circuit by-pass control button for generating a stimulation signal.

15. The sequential electrical stimulator according to claim 6 wherein said at least a pair of electrodes composed of rubber-carbon composite for stimulating dysphagic patients placed on the skin under the chin in the midline (submental region) separated by a distance of 0.5–1.5 cm.

16. The sequential electrical stimulator according to claim 6 wherein said at least a pair of electrodes composed of rubber-carbon composite for stimulating the thyrohyoid muscle and placed bilaterally on the skin at the wings of the larynx (thyroid cartilage) with the upper edge of the electrodes below the hyoid bone.

17. The sequential electrical stimulator according to claim 6 wherein said at least a pair of electrodes composed of rubber-carbon composite for stimulating the thyrohyoid muscle placed bilaterally on the skin at the wings of the larynx (thyroid cartilage) separated by a distance of 0.5–1.5 cm with the upper edge of the electrodes below the hyoid bone.

18. The sequential electrical stimulator according to claim 6 wherein said at least a pair of electrodes composed of rubber-carbon composite for stimulating the masseter muscles placed bilaterally on the skin of the cheeks in the region of the ascending ramus of the mandible.

\* \* \* \* \*

UNITED STATES PATENT AND TRADEMARK OFFICE
CERTIFICATE OF CORRECTION

PATENT NO. : 6,484,053 B2
DATED : November 19, 2002
INVENTOR(S) : Leelamanit et al.

It is certified that error appears in the above-identified patent and that said Letters Patent is hereby corrected as shown below:

Drawings,
Please delete Figures 1-8 and substitute the attached Figures 1-8.

Signed and Sealed this

Eighteenth Day of March, 2003

JAMES E. ROGAN
*Director of the United States Patent and Trademark Office*